United States Patent [19]

Sturrock

[11] Patent Number: 5,146,914
[45] Date of Patent: Sep. 15, 1992

[54] REUSABLE, VALVED, TRANSPARENT, POCKET RESUSCITATION MASK

[76] Inventor: Sheldon Sturrock, 56 Lanstaff Road West, Richmond Hill, Ontario, Canada, L4C 6N2

[21] Appl. No.: 694,823

[22] Filed: May 2, 1991

[30] Foreign Application Priority Data

Mar. 3, 1990 [CA] Canada ................... 2016005

[51] Int. Cl.$^5$ ............. A61M 16/00; A62B 18/02; A62B 18/08
[52] U.S. Cl. .................. 128/203.11; 128/202.29; 128/205.25; 128/206.26
[58] Field of Search .............. 128/202.28, 202.29, 128/203.11, 205.25, 206.21, 206.24, 206.26, 206.28

[56] References Cited

U.S. PATENT DOCUMENTS

| | | | |
|---|---|---|---|
| 3,252,457 | 5/1966 | Monaco et al. | 128/203.11 |
| 3,695,264 | 10/1972 | Laeral | 128/202.28 |
| 4,106,502 | 8/1978 | Wilson | 128/203.11 |
| 4,807,617 | 2/1989 | Nesti | 128/205.12 |
| 4,811,730 | 3/1989 | Milano | 128/202.29 |
| 4,834,085 | 5/1989 | Webster, II | 128/202.29 |
| 4,873,972 | 10/1989 | Magidson et al. | 128/206.24 |
| 4,886,057 | 12/1989 | Nave | 128/202.28 |
| 4,991,575 | 2/1991 | Fitz | 128/202.28 |

FOREIGN PATENT DOCUMENTS

| | | | |
|---|---|---|---|
| 0252618 | 6/1987 | European Pat. Off. | 128/205.24 |
| 2402192 | 7/1975 | Fed. Rep. of Germany | 128/205.13 |
| 799225 | 8/1958 | United Kingdom | 128/205.24 |

*Primary Examiner*—Edgar S. Burr
*Assistant Examiner*—Kimberly L. Asher
*Attorney, Agent, or Firm*—Bell, Seltzer, Park & Gibson

[57] ABSTRACT

A reusable resuscitation mask is provided with a semi-rigid shell having a centrally disposed aperture, an inner membrane or liner having a one-way valve adapted for insertion into the central aperture of the shell, and an inflatable cushion surrounding a peripheral portion of the inner membrane. The membrane comes in contact with a patient during use and may be disposed of, whereas the semi-rigid shell does not come in contact with the patient and may reused many times.

2 Claims, 4 Drawing Sheets

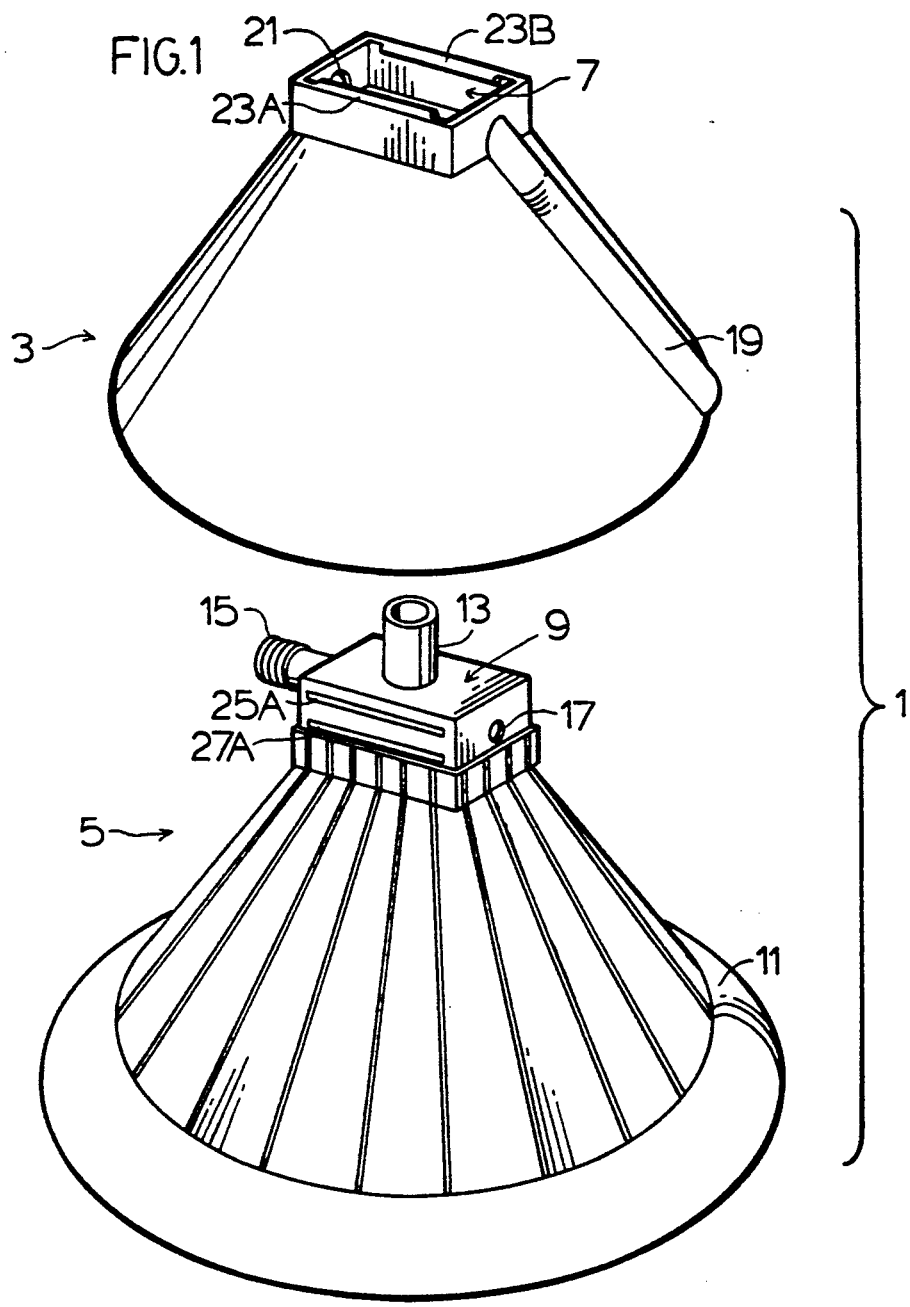

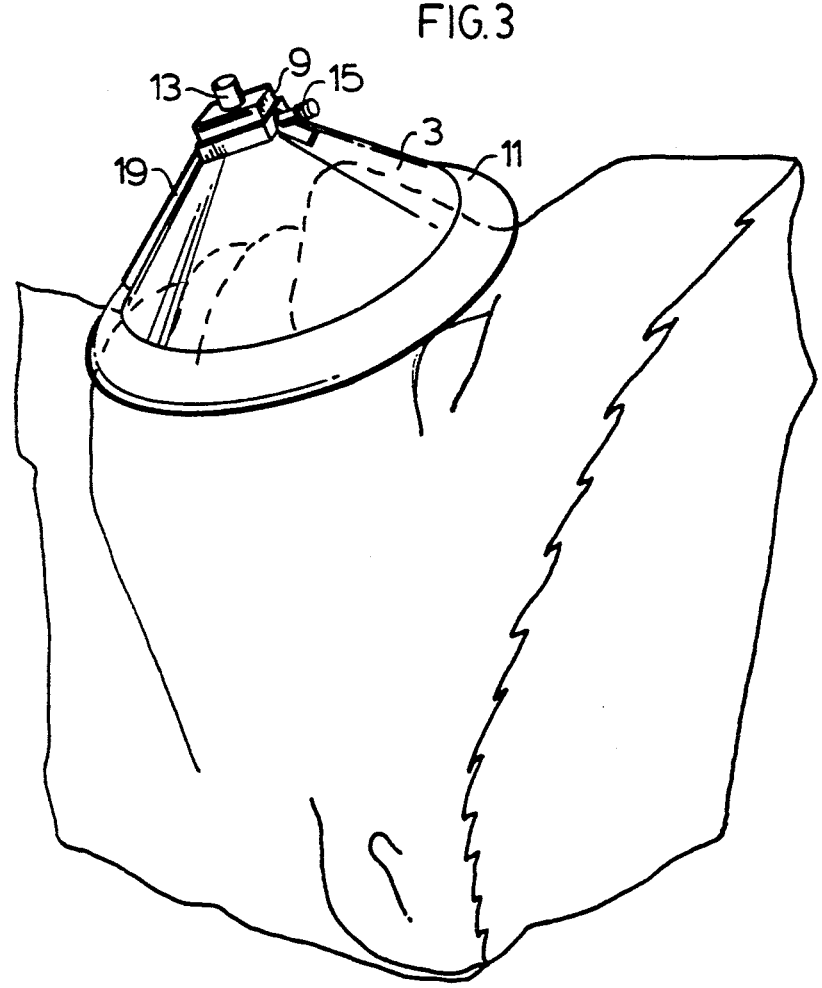
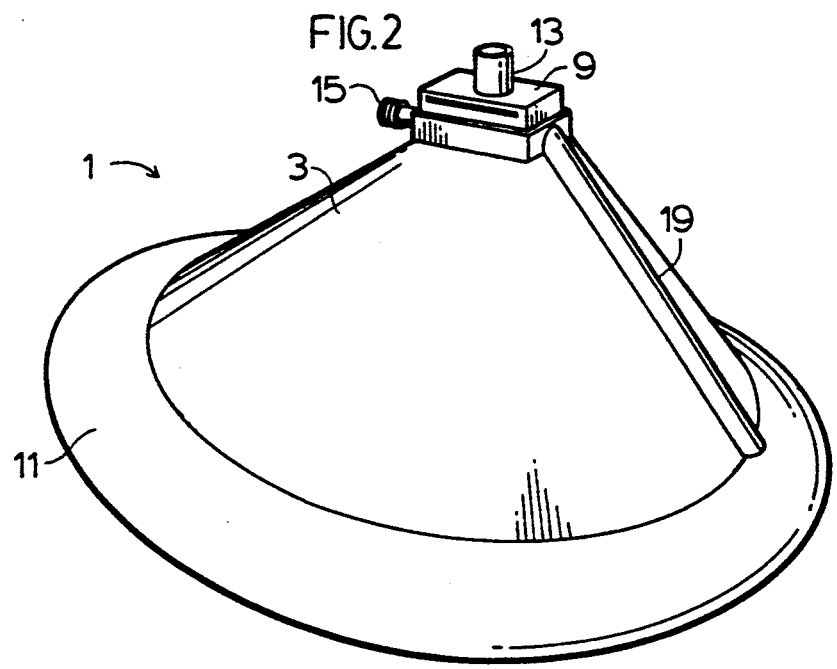

REUSABLE, VALVED, TRANSPARENT, POCKET RESUSCITATION MASK

FIELD OF THE INVENTION

The present invention relates in general to resuscitation masks, and more particularly to a reusable pocket mask having a disposable inner membrane and an easily portable semi-rigid shell.

BACKGROUND OF THE INVENTION

Pocket resuscitation masks are well known in the medical and paramedic fields for providing protection to a person giving mouth to mouth resuscitation of a patient. One such prior art pocket mask incorporates a semi-rigid portion with inflated cushions for surrounding the patient's mouth and nose. This prior art mask is required to be thoroughly cleaned and sterilized after each usage.

One disadvantage of requiring complete cleaning and sterilization results from the fact that such pocket masks are often used in communal situations (i.e. emergency wards, ambulances, etc.) in which there may be some uncertainty as to how thoroughly the pocket mask has been cleaned by another person. Failure to clean and sterilize the pocket mask can result in substantial risk of contracting disease, etc. This often results in expensive pocket masks being simply disposed of instead of being cleaned and reused.

Furthermore, creases and folds in the design of this prior art pocket mask can frequently make thorough cleaning and sterilization of the mask extremely difficult. The prior art mask is also typically of unwieldy size, and therefore difficult to fold for easy pocket carrying.

Another disadvantage of such prior art pocket masks is that in some instances, they are available in one size only such that a mask which may be suitable for resuscitating an adult would be unsuitable for resuscitating a small child.

SUMMARY OF THE INVENTION

According to the present invention, a reusable pocket mask is provided comprising a semi-rigid shell having a centrally disposed aperture therein. The semi-rigid shell is designed for easy folding and transportation and may be reused many times without requiring cleaning and sterilization. A disposable inner membrane or liner is provided having a valve portion adapted for removable insertion into the centrally disposed aperture. An inflatable cushion is provided around a peripheral portion of the liner and is adapted to surround the mouth and nose of a patient to be resuscitated such that the cushion forms the only point of contact with the patient. The valve is of one-way design such that a rescuer or paramedic can force air into the lungs of the patient through the valve while any exhalation from the patient is channeled through an exhaust port, thereby isolating the rescuer from any contagious disease, virus, vomit, etc. After use with the patient, the liner can be easily detached from the rigid semi-shell and disposed of. A new liner can then be reinserted into the shell for assembling the mask. The cushion portion is thus ready to be inflated at the time of use.

By reusing the semi-rigid shell, there are substantial cost savings over prior art pocket masks, which, as discussed above, are often disposed of due to the difficulties in cleaning such masks after use, and the inherent uncertainty as to whether or not a mask cleaned by someone else has been adequately sterilized.

The pocket mask of the present invention is collapsible to extremely small proportions due to the fact that the cushion is not inflated until required for actual use. Thus the mask may be easily stored in the glove compartment of a vehicle, in a paramedic's pocket, first-aid kit, etc.

According to the present invention, there is provided a resuscitation mask comprising a reusable shell having an aperture disposed centrally thereof and a disposable liner forming a generally conical space adapted to surround the mouth and nose of a patient while isolating the patient from said shell, said liner being provided with a one-way valve detachably connected to said aperture for passing air from a resuscitator into the lungs of said patient and passing exhaust air from said patient into the atmosphere, whereby said shell may be repeatedly reused as a result of being isolated from the patient.

BRIEF DESCRIPTION OF THE DRAWINGS

A preferred embodiment of the invention will be described in greater detail below with reference to the following drawings in which:

FIG. 1 is a perspective view of a semi-rigid shell and inflatable membrane liner according to the preferred embodiment;

FIG. 2 shows the semi-rigid shell and inflatable liner assembled for operation;

FIG. 3 shows the assembled pocket mask of the preferred embodiment in the position for use on a patient;

DETAILED DESCRIPTION OF THE PREFERRED EMBODIMENT

Figure 4:
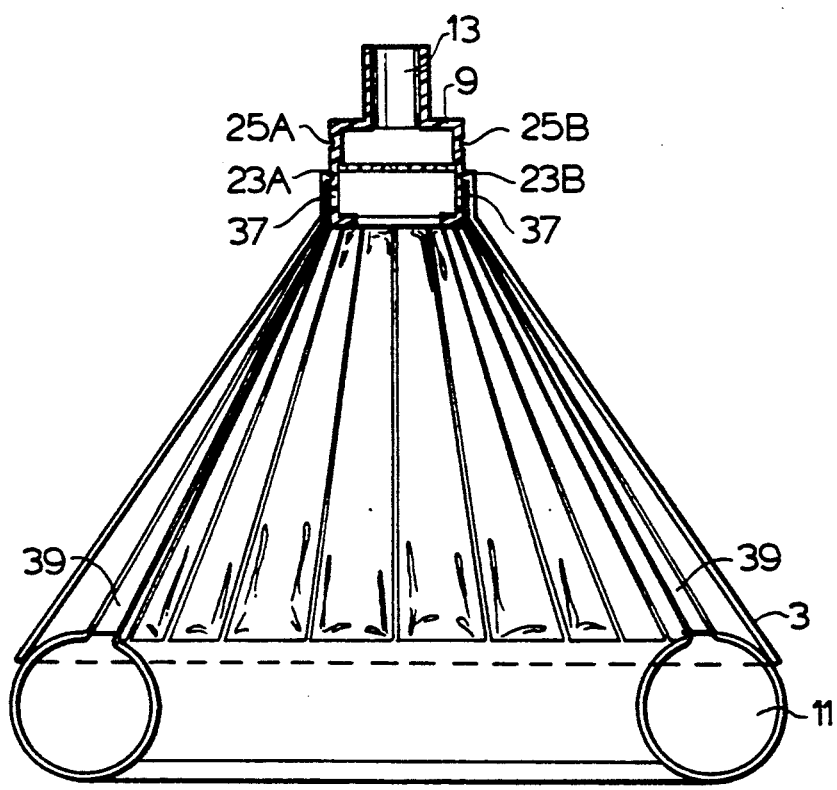
FIG. 4 is a cross section view of the assembled pocket mask of the preferred embodiment.

FIGS. 1 and 2 illustrate the pocket mask 1 of the preferred embodiment comprising a semi-rigid shell 3 and an inner liner or membrane 5. The shell 3 incorporates a centrally disposed aperture 7 surrounded by a rectangular housing. The inner liner 5 includes a one-way valve 9 of rectangular shape adapted to fit within the aperture 7 of the semi-rigid shell 3. The liner forms a generally conical space bounded by a peripherally disposed annular inflatable cushion 11 adapted to fit snugly over the mouth and nose of a patient requiring resuscitation, as shown in FIG. 3.

The valve 9 further includes an inlet port 13, an oxygen inlet 15 and an exhaust port 17.

The semi-rigid shell 3 is deformed in a generally quonset-shape to form an exhaust channel 19 extending between an inner surface of shell 3 and the outer surface of liner 5 from exhaust port 17 to a distal portion the mask proximate the patient's chin, as shown in FIG. 3.

The shell 3 is additionally provided with an aperture 21 adapted to receive the oxygen inlet 15 of the valve 9.

Turning to FIG. 4, a cross sectional view of the assembled pocket mask is shown with the valve 9 connected within aperture 7. In particular, the shell 3 is shown provided with a pair of ridges 23A and 23B adapted for cooperative engagement with one of first and second pairs of cooperatively shaped grooves 25A, 25B and 27A, 27B (see FIG. 8). The cooperatively shaped ridges and grooves function to detachably connect the valve 9 within the aperture 7 of shell 3 in one of an upper or lower position. The valve 9 is shown in FIG. 4 connected in the upper or operative position for maintaining cushion 11 inflated, as will be discussed in greater detail below.

Figure 5:
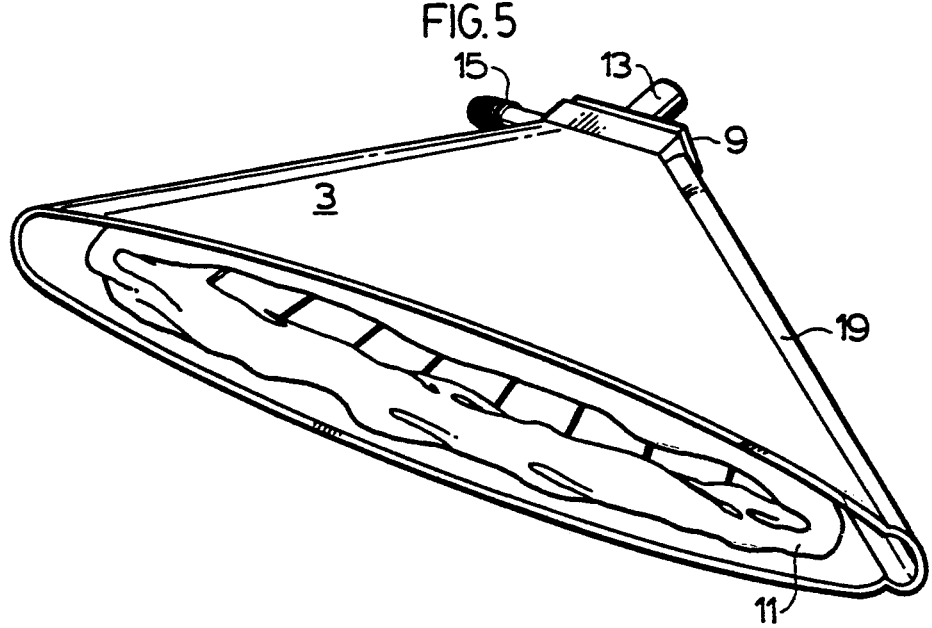
FIG. 5 is a perspective view of the assembled pocket mask prior to inflation of the cushion portion.

FIG. 5 is a perspective view of the assembled pocket mask prior to inflation of the cushion 11.

Figure 6:
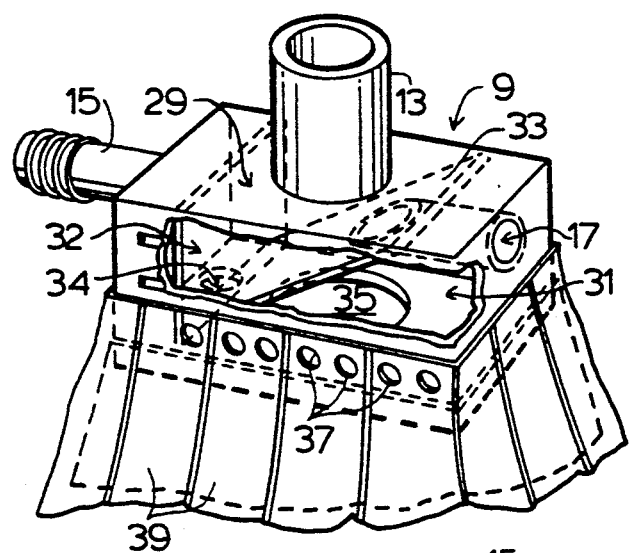
FIG. 6 is a detailed perspective, partly cut away view of the one-way valve according to the preferred embodiment.

The construction of valve 9 is shown in greater detail below with reference to FIGS. 6 and 7, comprising upper and lower chambers 29 and 31 respectively, separated by a pivoting flapper 33.

Figure 7:
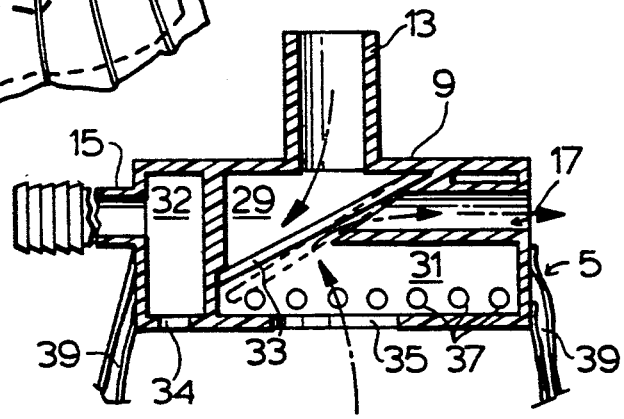
FIG. 7 is a longitudinal cross-section view of the one-way valve shown in FIG. 6.

The flapper 33 is adapted to move from a first position shown in dashed outline with reference to FIG. 7, by which exhaust port 17 is blocked such that air introduced within the inlet port 13 passes from upper chamber 29 into lower chamber 31 and therefrom via an opening 35 into the conical space surrounding the patient's mouth and nose. In the position discussed, air may be channeled from a resuscitator into the lungs of the patient.

In the second position shown in solid lines with reference to FIG. 7, the end portion of flapper 33 rests against an undercut ledge of the upper chamber 29 while at the same time opening the exhaust port 17. Thus, in the position of flapper 33 shown in solid lines, exhausted air from the patient is prevented from flowing back through inlet 13 and is instead channeled through opening 35, chamber 31 to exhaust port 17 and therefrom via exhaust channel 19 to a remote portion of the mask proximate the patient's chin.

An additional chamber 32 is provided for introducing oxygen received via oxygen inlet 15 into the conical space provided by liner 5 through an additional opening 34. Of course, in the event of no oxygen source being connected to inlet 15, a plug or other sealing means is required to prevent exhaust or inlet air escaping through the inlet 15 via opening 34.

According to an additional aspect of the invention, a plurality of small circular apertures 37 are provided in side walls of the valve 9 between the lower chamber 31 and a corresponding plurality of air passages 39 within liner 5. The air passages 39 extend from the apertures directly into the inflatable cushion 11, as shown best with reference to FIG. 4.

Figure 8:
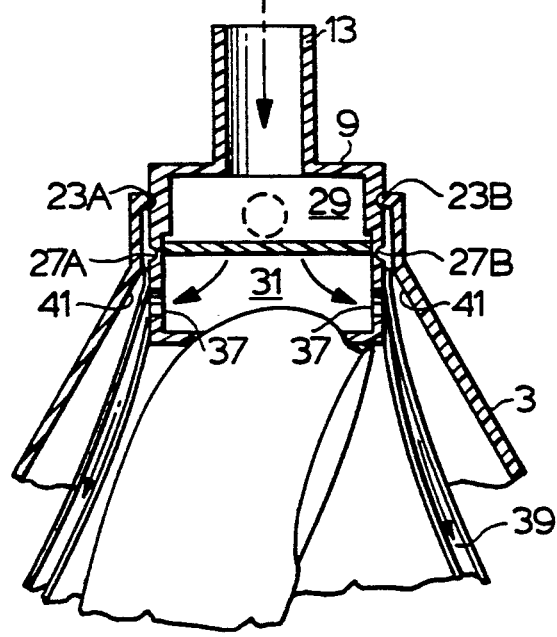
FIG. 8 is a lateral cross section view of the valve shown in FIG. 6 illustrating a method for inflating the cushion portion of the inner liner.

In operation, with reference to FIG. 8, by positioning valve 9 in the lower position within aperture 7 (i.e. with ridges 23A, 23B locked within grooves 25A, 25B), and by plugging the opening 35 with a finger, blowing air into the inlet 13 results in flapper 33 falling to the lower position (i.e. dashed outline in FIG. 7) so as to block exhaust port 17 such that the air travels from upper chamber 29 into lower chamber 31 and therefrom via apertures 37 into the channels 39 for inflating the cushion 11. Once the cushion is fully inflated, the valve 9 is pushed further into aperture 7 such that the ridges 23A, 23B engage with corresponding grooves 27A, 27B, as shown in FIG. 4. In this "upper" position of the valve 9 within aperture 7, a pair of shoulders 41 (FIG. 8) of the shell 3 are caused to bear down on the apertures 37 for effectively blocking the apertures such that the cushion 11 is maintained in an inflated state.

In summary, according to the present invention, a reusable pocket resuscitation mask is provided whereby the semi-rigid shell 3 may be reused without prior cleaning and sterilization, in contrast with the known prior art. Furthermore, the mask may be folded and easily transported with cushion 11 deflated. This is an attractive feature for police, lifeguards or other users who require compact storage of the mask when not in use.

The mask described herein with reference to FIGS. 1–8 relates to a preferred embodiment. Other modifications or embodiments are possible within the sphere and scope of the present invention. For example, the disposable liner 3 may be fabricated in various sizes to suit different sizes of patients (e.g. large adults to small children), and may be used with the identical reusable semi-rigid shell. In addition, other varieties of one-way valve 9 may be utilized provided that the valve serves the same function of separating the inlet and exhaust chambers 29 and 31 to prevent backflow from the patient to the resuscitator.

These and other embodiments are believed to be within the scope of the claims appended hereto.

I claim:

1. A resuscitation mask comprising a reusable shell having an aperture disposed centrally thereof and a disposable liner forming a generally conical space adapted to surround the mouth and nose of a patient while isolating the patient from said shell, said liner being provided with a one-way valve detachably connected to said aperture for passing air from a resuscitator into the lungs of said patient and passing exhaust air from said patient into the atmosphere, whereby said shell may be repeatedly reused as a result of being isolated from the patient, wherein said valve further comprises upper and lower chambers separated by a pivoting flapper, an inlet port connected to said upper chamber, an opening from said lower chamber into said generally conical space, and an exhaust port connected to said lower chamber, said flapper being adapted to pivot from a first position for blocking said exhaust port and allowing the passage of air from said upper to said lower chamber and therefrom through said opening into said conical space, and a second position for preventing air passage from said lower to said upper chamber and allowing the passage of exhaust air from said conical space through said opening and into the atmosphere via said exhaust port, further comprising a plurality of small apertures in said valve between said lower chamber and a corresponding plurality of air passages within said liner, said air passages extending from said apertures to said cushion for inflating said cushion.

2. The resuscitation mask of claim 1 further comprising a pair of ridges on said aperture and first and second pairs of cooperatively shaped indentations on said valve for detachably connecting said liner to said aperture in respective upper and lower positions, said plurality of small apertures remaining unobstructed when said liner is connected in said upper position for inflating said cushion, and said apertures being obstructed by said valve when said liner is connected in said lower position for maintaining said cushion inflated.

* * * * *